(12) United States Patent
Wiand

(10) Patent No.: US 10,628,672 B2
(45) Date of Patent: Apr. 21, 2020

(54) METHOD AND SYSTEM FOR AERIAL DETECTION AND MAPPING OF AQUATIC SPECIES

(71) Applicant: Zero Gravity Digital, LLC, Bloomfield Hills, MI (US)

(72) Inventor: Dennis Wiand, Bloomfield Hills, MI (US)

(*) Notice: Subject to any disclaimer, the term of this patent is extended or adjusted under 35 U.S.C. 154(b) by 122 days.

(21) Appl. No.: 15/914,062

(22) Filed: Mar. 7, 2018

(65) Prior Publication Data

US 2018/0260627 A1 Sep. 13, 2018

Related U.S. Application Data

(60) Provisional application No. 62/468,559, filed on Mar. 8, 2017.

(51) Int. Cl.
| | |
|---|---|
| G06K 9/00 | (2006.01) |
| G01N 33/00 | (2006.01) |
| H04N 5/76 | (2006.01) |
| G06K 9/62 | (2006.01) |
| G01S 17/89 | (2020.01) |
| A01M 21/04 | (2006.01) |
| H04N 5/77 | (2006.01) |
| G01V 8/10 | (2006.01) |
| G01N 21/84 | (2006.01) |
| G01N 21/25 | (2006.01) |
| G01N 21/17 | (2006.01) |
| G01N 21/359 | (2014.01) |
| G01N 21/85 | (2006.01) |

(52) U.S. Cl.
CPC ....... *G06K 9/00657* (2013.01); *A01M 21/043* (2013.01); *G01N 33/0098* (2013.01); *G01S 17/89* (2013.01); *G01V 8/10* (2013.01); *G06K 9/0063* (2013.01); *G06K 9/6289* (2013.01); *H04N 5/76* (2013.01); *H04N 5/772* (2013.01); *G01N 21/25* (2013.01); *G01N 21/359* (2013.01); *G01N 21/84* (2013.01); *G01N 21/85* (2013.01); *G01N 2021/1793* (2013.01); *G01N 2021/1797* (2013.01); *G01N 2021/8466* (2013.01)

(58) Field of Classification Search
CPC combination set(s) only.
See application file for complete search history.

(56) References Cited

U.S. PATENT DOCUMENTS

| | | | |
|---|---|---|---|
| 7,068,816 B1* | 6/2006 | Knoblauch | A01B 79/005 348/144 |
| 2012/0237083 A1* | 9/2012 | Lange | G06K 9/00805 382/103 |
| 2012/0320203 A1* | 12/2012 | Liu | G01C 11/04 348/144 |
| 2015/0339323 A1* | 11/2015 | Schaeffer | H04W 4/029 382/305 |
| 2016/0018559 A1* | 1/2016 | Levien | G01V 8/02 250/255 |

* cited by examiner

*Primary Examiner* — Alex Kok S Liew
(74) *Attorney, Agent, or Firm* — Traverse Legal, PLC

(57) ABSTRACT

What is provided is a method and system for more precisely, accurately, and reliably detecting aquatic species, namely infestations of invasive aquatic plants. The system and methods disclosed herein allow for a more effective determination of a treatment plan to reduce any potential negative impact on the aquatic ecology and to minimize any unnecessary human exposure to toxic chemicals.

14 Claims, 8 Drawing Sheets

METHOD AND SYSTEM FOR AERIAL DETECTION AND MAPPING OF AQUATIC SPECIES

PRIORITY CLAIM

This patent application is a Non-Provisional Patent Application and claims priority under 35 U.S.C. 119(e) to U.S. Provisional Patent Application Ser. No. 62/468,559, titled "SYSTEM AND METHODS FOR AERIAL DETECTION AND MAPPING OF AQUATIC SPECIES," filed Mar. 8, 2017. The entire disclosure of the aforementioned patent application is incorporated by reference as if fully stated herein.

FIELD

The present invention generally relates to method and system for aerial detection and mapping of aquatic species. More particularly, the present invention relates to aerial detection and mapping of invasive aquatic plants using an unmanned aerial vehicle (UAV).

BACKGROUND

Certain invasive aquatic species grow so prodigiously that they pose threats to naturally occurring bodies of water, such as lakes, reservoirs, rivers, and stream, and to native aquatic plants and animals. In addition, people find such proliferation of invasive aquatic species to be unsightly and problematic to their own enjoyment of the water as they may prevent people from entering the water. Examples of some commonly found invasive aquatic plants include Eurasian Water milfoil, Curly-Leaf Pondweed, Fanwort, Hydrilla, and Phragmites. In order to effectively treat and prevent infestation of invasive aquatic species, it is critical to be able to accurately detect and map the locations of the species in various bodies of water. Common ways of treating invasive aquatic plant infestations involves the use of chemical applications in the water.

Currently, several techniques are used to identify and map the locations of invasive aquatic species. First, invasive aquatic plants are observed and detected at the water level using viewing scopes and GPS. If the water is too deep to allow plants to be observed directly, sampling rakes are used to bring plants up from the bottom of the water, particularly those plants that may be growing beneath dominant plants or boat launches. Another commonly used technique involves collecting data along transect lines laid out perpendicular to the shore using rake tosses in four directions at each transect point to detect any plants intersecting the transect lines that are then recorded. Specific algorithms are then used to interpolate the collected data. As such, this technique can be very time-consuming and inefficient.

Yet another commonly used technique for identifying and mapping the locations of invasive aquatic species involves the use of sonar through a BioBase™ sonar transducer. In this technique, data collected from bodies of water using these types of transducers needs to be interpolated using algorithms in order to estimate plant biomass. Due to difficulties calibrating sensors and user operation outside of manufacturer specifications, false positives of plant mass are typically found when the data is uploaded to and visualized by third party mapping features. In addition, the maximum angle of view on a BioBase™ sonar transducer depth finder is only 20 degrees, while the recommended transect distance provided by BioBase™ is 15 feet on lakes having less than 30 acres in surface area and 82 feet on lakes having greater than 30 acres in surface area. This presents limitations on the areas of coverage for aquatic plant detection, particularly for bodies of water of a certain size and depth. Lastly, the BioBase™ sonar transducer may only be used at a maximum speed of 7 miles/hour and typically works better at speeds closer to 3 miles/hour. Thus, the BioBase™ sonar transducer results in a very time-consuming technique for gathering data invasive aquatic species.

Consequently, there is a need for a more precise, reliable, and accurate way for detecting and mapping aquatic species, namely infestations of invasive aquatic plants.

SUMMARY

What is provided is a method and system for more precisely, accurately, and reliably detecting and mapping aquatic species, namely infestations of invasive aquatic plants. The system and methods disclosed herein allow for a more effective determination of a treatment plan to reduce any potential negative impact on the aquatic ecology and to minimize any unnecessary human exposure to toxic chemicals.

In exemplary embodiments, the method for visually detecting and mapping the presence of a target species located beneath the surface of a body of water comprises calibrating a camera and at least one sensor on an aerial platform to record light wave reflectance values from the target species; scanning, using the aerial platform, a littoral zone of the body of water to identify the location of the target species; capturing, using the camera, at least one image or video of the body of water; recording, using the at least one sensor, data corresponding to the at least one image or video on the aerial platform; detecting the presence of the target species in the body of water and if the target species is present in the body of water obtaining a ground truth sample of the target species; transmitting the at least one image or video from the aerial platform to a first third-party application; assembling and processing the at least one image or video to create an ortho-mosaic, wherein the ortho-mosaic displays the precise location of the target species; and uploading the at least one image or video to a second third-party application to generate a map showing the location of the target species in the body of water.

In exemplary embodiments, the system for visually detecting and mapping the presence of a target species located beneath the surface of a body of water comprises an aerial platform, wherein the aerial platform is configured to scan a littoral zone of the body of water to identify the location of the target species; a camera and at least one sensor on the aerial platform, wherein the camera is configured to capture at least one image or video of the body of water and wherein the at least one sensor is configured to record data corresponding to corresponding to the at least one image or video; and a controller in direct communication with the aerial platform, wherein the controller is configured to control the position and orientation of the aerial platform with regard to the body of water and to display data, images, and videos received from the aerial platform.

These and other features, advantages, and object of the application disclosed herein will be further understood and appreciated by those skilled in the art by reference to the following specification, claims, and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Subject matter is particularly pointed out and distinctly claimed in the concluding portion of the specification. Claimed subject matter, however, as to structure, organization and method of operation, together with objects, features, and advantages thereof, may best be understood by reference to the following detailed description if read with the accompanying drawings in which:

DETAILED DESCRIPTION

Figure 1:
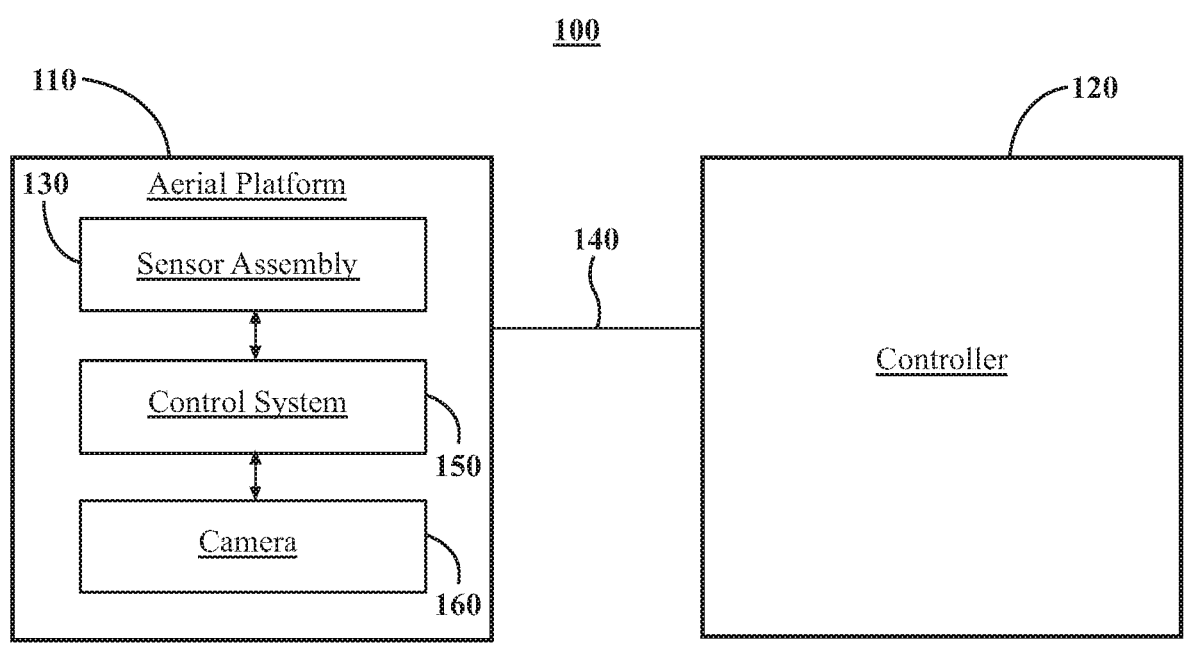
FIG. 1 is a block diagram of an exemplary system for executing one or more of the methods described herein, including detecting and mapping aquatic plants.

In the following detailed description, numerous specific details are set forth in order to provide a thorough understanding of the examples as defined in the claimed subject matter, and as an example of how to make and use the examples described herein. However, it will be understood by those skilled in the art that claimed subject matter is not intended to be limited to such specific details, and may even be practiced without requiring such specific details. In other instances, well-known methods, procedures, and components have not been described in detail so as not to obscure the examples defined by the claimed subject matter.

Unless specifically stated otherwise, as apparent from the following discussion, it is appreciated that throughout this specification a computing platform includes, but is not limited to, a device such as a computer or a similar electronic computing device that manipulates and/or transforms data represented by physical, electronic, and/or magnetic quantities and/or other physical quantities within the computing platform's processors, memories, registers, and/or other information storage, transmission, reception and/or display devices. Accordingly, a computing platform refers to a system, a device, and/or a logical construct that includes the ability to process and/or store data in the form of signals. Thus, a computing platform, in this context, may comprise hardware, software, firmware and/or any combination thereof. Where it is described that a user instructs a computing platform to perform a certain action, it is understood that "instructs" may mean to direct or cause to perform a task as a result of a selection or action by a user. A user may, for example, instruct a computing platform embark upon a course of action via an indication of a selection, including, for example, pushing a key, clicking a mouse, maneuvering a pointer, touching a touch pad, touching a touch screen, acting out touch screen gesturing movements, maneuvering an electronic pen device over a screen, verbalizing voice commands, and/or by audible sounds. A user may include an end-user.

According to the methods described herein, a computing device can automatically process and analyze multiple types of data to accurately identify and map out the locations of aquatic plants in bodies of water. Data can include real-time or near real-time data produced by a UAV, commonly known as a drone, unmanned aircraft system (UAS), unmanned-aircraft vehicle system (UAVS), or remotely piloted aerial vehicle (RPAV) and devices that can be manually adjusted. A UAV may be an airplane or helicopter, for example, radio-controlled by a human utilizing a handheld radio controller. Data can also be produced by a flying camera, flying robot, satellite, airplane, and/or ground-located sensor.

Flowcharts, also referred to as flow diagrams by some, are used in some figures herein to illustrate certain aspects of some examples. Logic they illustrate is not intended to be exhaustive of any, all, or even most possibilities. Their purpose is to help facilitate an understanding of this disclosure with regard to the particular matters disclosed herein. To this end, many well-known techniques and design choices are not repeated herein so as not to obscure the teachings of this disclosure.

Throughout this specification, the term "system" may, depending at least in part upon the particular context, be understood to include any method, process, apparatus, and/or other patentable subject matter that implements the subject matter disclosed herein. The subject matter described herein may be implemented in software, in combination with hardware and/or firmware. For example, the subject matter described herein may be implemented in software executed by a hardware processor.

The terms "water," "body of water" and "bodies of water" as used herein, refer to naturally occurring surface water such as oceans, lakes, streams, seas, gulfs, estuaries, rivers, and man-made bodies of water such as canals, reservoirs, ponds, and the like. The water may be fresh or saltwater.

The term "chemical applicator" as used herein, refers to an object for administrating a chemical treatment to a body of water. In some embodiments, the chemical treatment is administered through a chemical applicator vessel. Examples of the types of chemicals administered to treat a body of water include, but are not limited to antifoams, biocides, pesticides, coagulants, disinfectants, corrosion inhibitors, oxidants, neutralizing agents, oxygen scavengers, pH conditioners, resin cleaners, algaecides, and scale inhibitors.

The method for detecting and mapping aquatic species disclosed herein is particularly beneficial when determining the amount of chemicals to apply to the water during treatment and the precise location of the of the applied chemicals in order to reduce potential negative impact on the aquatic ecology. By using a UAV with the current methods, the risk of any unnecessary exposure to toxic chemicals for the individuals administering the chemicals in the water is significantly reduced, if not prevented altogether.

Referring to FIG. 1, FIG. 1 shows a block diagram of an exemplary system 100 for executing one or more of the methods described herein, including detecting and mapping aquatic plants. The system 100 includes an aerial platform 110 and a controller 120. In some embodiments, the aerial platform 110 is an unmanned vehicle-based system, such as a UAV, while in other embodiments, the aerial platform 110 is a manned airplane or helicopter. Generally speaking, the term "unmanned" means the aerial platform 110 does not have an on-board pilot.

The aerial platform 110 includes a camera 160 configured to capture images and/or videos of a real-world scene; a sensor assembly 130 configured to capture data, images, and/or video of a real-world scene, and a control system 150 in communication with the aerial platform 110. Any information that is collected by the sensor assembly 130 is stored within the sensor assembly 130 for subsequent analysis. The information may also be transmitted to a ground station (not shown) for processing.

In the embodiment shown in FIG. 1, the controller 120 is a computer system configured to display images and/or video. The aerial platform 110 may be coupled to the controller 120 via a link 140. The link 140 may be used by the controller 120 to command the aerial platform 110 (e.g., to move and/or to capture images or video) and/or may be used by the aerial platform 110 to transmit images or video the controller 120. In an embodiment, the link 140 is wireless. In an embodiment, the link 140 includes cellular links or networks. In some embodiments, the controller 120 comprises a smartphone, a tablet, a smart watch, or the like.

In some examples, the controller 120 may transmit signals to the aerial platform 110 to cause the aerial platform 110 to move to a desired position and to capture images and/or videos of the surrounding environment. These signals may be transmitted by the controller 120 in response to user input from a human operator of the controller 120.

Figure 2:
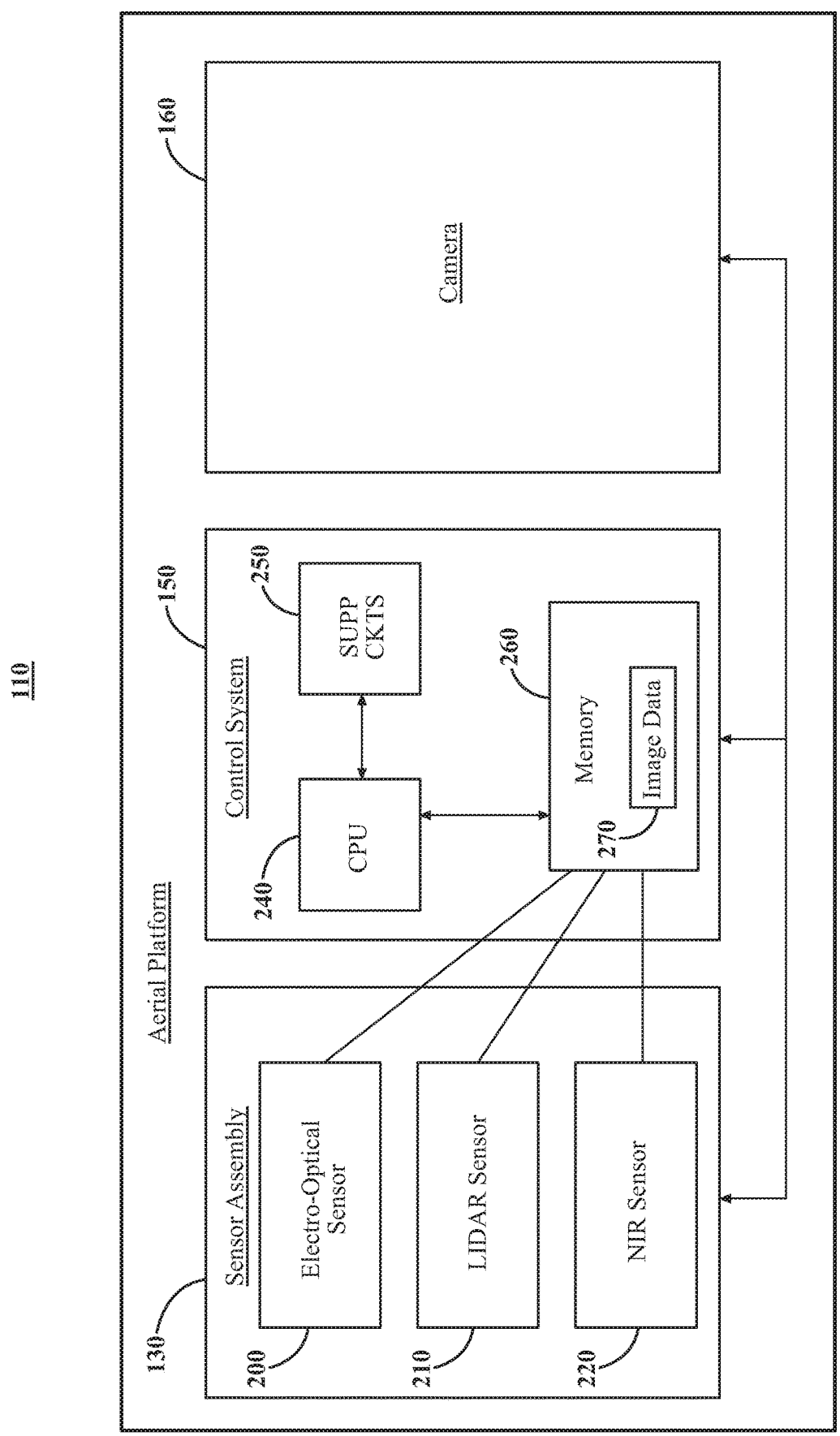
FIG. 2 is a block diagram of an exemplary sensor assembly mounted to and carried by the aerial platform of FIG. 1.

Referring to FIG. 2, FIG. 2 shows a block diagram of an exemplary sensor assembly 130 mounted to and carried by the aerial platform 110 of FIG. 1. Exemplary sensors suitable for use with the embodiments disclosed herein include location sensors (e.g., global positioning system (GPS) sensors), vision sensors (e.g. imaging devices capable of detecting visible, infrared, or ultraviolet light, such as cameras), proximity or range sensors (e.g., ultrasonic sensors, Light Imaging, Detection, and Ranging (LIDAR) sensors, flight or depth cameras), or field sensors (e.g., magnetometers, electromagnetic sensors). Any suitable number and combination of sensors can be used, such as one, two, three, or more sensors. Sensors of different types may measure different types of signals or information and/or utilize different types of measurement techniques to obtain data.

In the embodiment shown in FIG. 2, the sensor assembly 130 comprises an electro-optical sensor (e.g., a video camera) 200, a Light Imaging, Detection, and Ranging (LIDAR) sensor 210, and a Near Infrared (NIR) sensor 220. In some examples, the electro-optical sensor is an RGB camera. The camera 160 may be used to generate 2D images of a 3D scene (e.g., an environment, one or more objects, etc.). The images generated by the camera 160 can represent the projection of the 3D scene onto a 2D image plane. By mounting each of the electro-optical sensor 200, the NIR sensor 220, and the LIDAR sensor 210 upon the sensor assembly 130, the electro-optical sensor 200, the NIR sensor 220, and the LIDAR sensor 210 may image objects, such as plants, located beneath the surface of the water at the same time. These objects are not readily visible by the human eye above the surface of the water.

In some examples, each of the electro-optical sensor 200, the NIR sensor 220, and the LIDAR sensor 210 may be separately used to image objects located beneath the surface of the water. In some examples, the NIR sensor 220 may just be used to image shallow rivers and streams, while the LIDAR sensor 210 may just be used to image shallow water and invasive plants located on the shore in order to obtain topographic and bathymetric data. The LIDAR sensor 210 and the NIR sensor 220 may be used to collect bathymetric data in order to determine the amount of chemical required, by acre-foot, which may need to be applied to manage the aquatic plant species. In other embodiments, the sensor assembly 130 comprises only the electro-optical sensor 200. In yet further embodiments, the sensor assembly 130 comprises the electro-optical sensor 200, the NIR sensor 220, the LIDAR sensor 210, and a multispectral sensor (not shown).

The sensor assembly 130 on the aerial platform 110 allows for imaging a complete view of the areas being mapped without the need to interpolate areas between intersect points. Thus, the sensor assembly 130 provides the mapping data capability. The field of view of the sensor assembly 130 may be the extent of the environment that is detectable by the sensor assembly 130. The field of view may be related to the angle of view, which may be measured by the angular extent of a given scene that is imaged by the sensor assembly 130. The angle of view of the sensor assembly 130 may be at an angle of less than or about 360°, 240°, 120°, 90°, 30°, or 10°. The field of view may be oriented vertically, horizontally, upward, downward, sideways, and the like relative to the aerial platform 110.

In some examples, the electro-optical sensor 200 with a polarizer may be positioned about 131 feet above the surface of the water and has an angle of view of about 92°. The effective angle of view with the electro-optical sensor 200 is about 50° without rectilinear distortion. Thus, the view results in about a 10,000-square foot area of coverage.

In some examples, the electro-optical sensor 200 is capable of acquiring an image with a resolution of between about 1.5 and 4 cm per pixel at a capture rate of 60 frames per second. The electro-optical sensor 200 may capture video and store or send the video in a number of formats (e.g., FLV, MPEG-1, MPEG-2, MPEG-4, RealMedia, Windows Media Video, QuickTime, AVI, Ogg, F4V, etc.). The electro-optical sensor 200 and the camera 160 may each record at various resolutions (e.g., 480p, 720p, 1080p, 4 k), depending on the embodiments. The electro-optical sensor 200 and the camera 160 may each record at various frame rates (e.g., 120, 60, 30, 24, 12, or fewer than 12 frames per second), depending on the embodiments. The electro-optical sensor 200 and the camera 160 may each be capable of capturing still images. The aerial platform 110 may be supported by hand, on a vehicle, or on a support, such as boom, tripod, or pole. In some examples, the sensor assembly 130 has a payload weight of about 262 g on the aerial platform 110.

The control system 150 is a computer system that may be affixed to the aerial platform 110 via a mount or casing (not shown). The output from the sensor assembly 130 is coupled to the control system 150 for storing the information from the sensor assembly 130 and the camera 160. The control system 150 comprises a CPU 240, support circuits 250, and memory 260. The CPU 240 may include one or more processors and associated processing elements and storage devices communicatively interconnected to one another by one or more busses or other communication mechanism for communicating information. The support circuits 250 may include cache, power supplies, input/output interfaces, and the like. The memory 260 may include random access memory (RAM) or other dynamic storage devices, for storing information and instructions to be executed by the CPU 240 and for storing temporary variables or other intermediate information during the use of the aerial platform 110 described herein. Such a computer system can also include read only memory (ROM) or other static storage device(s) for storing static information and instructions for the processor(s). A storage device, such as a hard disk or solid state memory can also be included for storing information and instructions, such as the instructions to compute stand determination from externally gathered data (e.g., image data), perform one or more analyses based on the gathered data, and to output an indication of the analyses and/or issue alerts. RAMs, ROMs, hard disks, solid state memories, and the like, are all examples of tangible computer readable media, which can be used to store the instructions for performing various techniques described herein. The memory 260 stores the image data 270 created by the sensor assembly 130.

The aerial platform 110 may transmit position and/or orientation data in addition to the image/video data captured by the sensor assembly 130. The position and/or orientation data may relate to position (absolute and/or relative), direction, and/or orientation of the aerial platform 110 and/or of an aquatic plant. The controller 120 generates and displays an image or video representing the captured real-world scene of the water according the received image signal. The image or video may be displayed in real-time or near real-time. The term "real-time" is generally synonymous with "near real-time," and typically refers to a lag of five seconds or less between the time at which the aerial platform 110 captures the image or video and the time at which the controller 120 displays the image or video.

Figure 3:
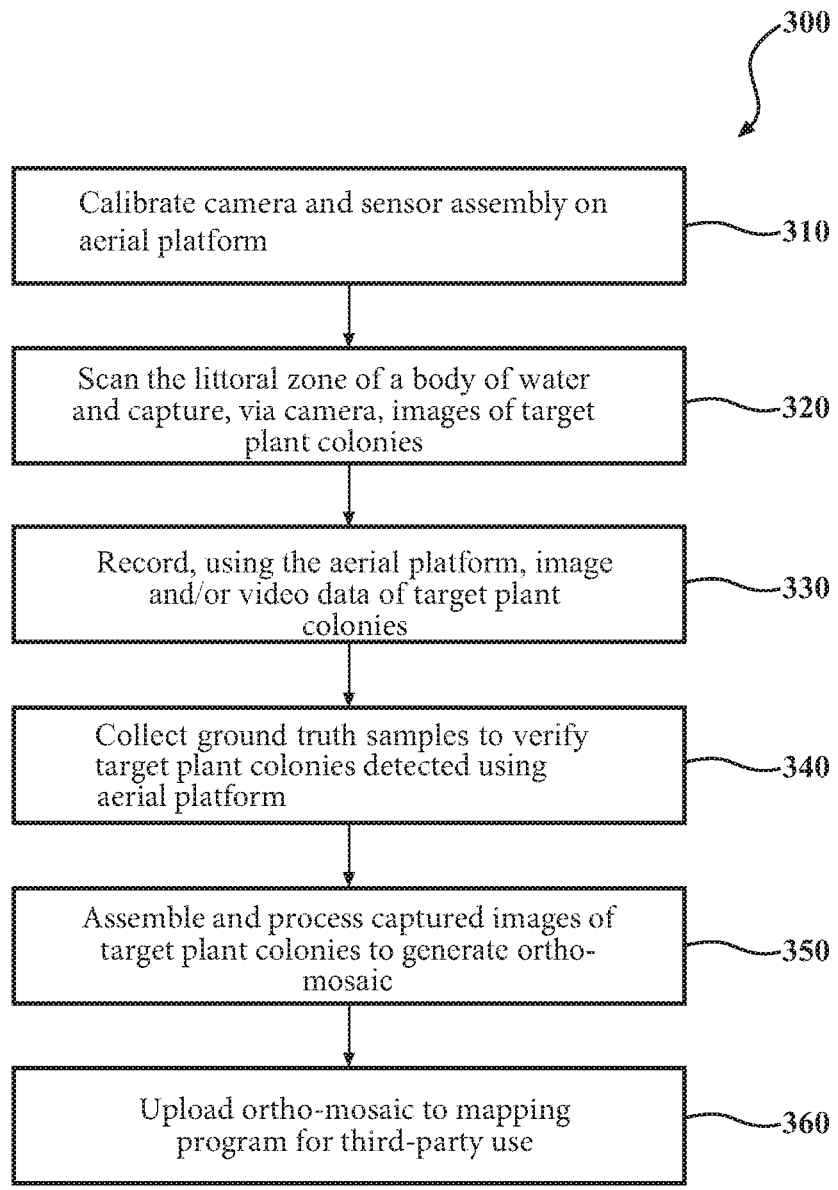
FIG. 3 is a flow chart of an exemplary method for visually detecting aquatic species in bodies of water.

Referring to FIG. 3, FIG. 3 shows a flow chart of an exemplary method 300 for visually detecting aquatic species in bodies of water. The method 300 may be implemented, in whole or in part, by the system 100 show in FIG. 1, and more particularly, by the aerial platform 110 and/or the controller 120 shown in FIGS. 1 and 2.

The method 300 begins when the controller 120 and the aerial platform 110 are calibrated to record light waves reflecting from objects, such as plants, located beneath the surface of the water, as shown in block 310. These objects are not readily visible by the human eye from above the surface. Calibrating the aerial platform 110 may include determining one or more angles of view associated with the sensor assembly 130 and calibrating the camera 160. For example, the electro-optical sensor 200 and/or the camera 160 may each be aimed down towards the body of water from the horizontal plane on which the aerial platform 110 is oriented at an angle of view of about 92 degrees. The electro-optical sensor 200 and/or the camera 160 are specifically calibrated to record reflectance values beneath the surface of the body of water being observed. One example of calibrating the reflectance value involves manually configuring the exposures values of the electro-optical sensor 200 to allow the aerial platform 110 to determine the location of the presence of plant colonies in the water that are not normally visible to the human eye.

As shown in block 320, the camera 160 scans the littoral zone of a body of water to identify and capture images of the location of aquatic plant colonies. In some embodiments, the littoral zone is the near shore area of the body of water to a depth (e.g., about 21 feet) where photosynthesis no longer takes place. As a result, the invasive aquatic plants may be readily identified for mapping, while the areas free of invasive aquatic plants may be quickly eliminated from mapping consideration.

In some examples, data collection by the aerial platform 110 is conducted using an autonomous flight plan grid, where the camera 160 is not activated in response to any commands from the controller 120. In other examples, data collection by the aerial platform 110 is conducted using a manual flight plan. In these examples, the controller 120 displays an image or video of a real-world scene captured by the camera 160. While the image or video is displayed, the controller 120 may detect user input.

In block 330, the aerial platform 110 records image and/or video data relating to the targeted plant species, which may comprise one or several invasive plants. As the image or video is being recorded by the aerial platform 110, the operator determines areas where target plant colonies exist and interrupts the image to record a geotagged image of the approximate center of a target plant colony for GPS location. In some examples, the geotagged image is captured from a nadir view. In some embodiments, the target plant species may be several plants in a complete macrophyte assessment. The geotagged images of the target plant colonies are captured with at least one sensor from the sensor assembly 130. The sensor is calibrated to record imagery of detail of the target plant colonies and surrounding area not normally visible to the human eye from above the surface of the water.

As shown in block 340, the aerial platform 110 then guides the collection of ground truth samples in order to verify the target plant colonies detected through images and video using the camera 160. Navigation to the target plant colonies may be aided by live video from the aerial platform 110. Current methods require a technician to conduct ground truthing by randomly deploying a rake to gather physical samples of the total littoral zone. No random sampling is required as the method 300 disclosed herein eliminates the need to gather data from areas free of plant colonies.

In one embodiment, the collection of samples on location may be conducted through rake sampling of plant colonies. In another embodiment, a buoy system may be implemented in open water to create ground reference points where ground reference points are not available. The system 100, though, allows for the reliable recording of data in open bodies of water without the availability of existing ground reference points.

Next, the geotagged images of the target plant colonies captured by the camera 160 are transmitted to a third-party application, such as PIX4D or a functionally similar application, for assembly into a high-resolution ortho-mosaic, as shown in block 350. The geotagged images provide an exact visual representation of the aquatic species present in a specific body of water. GPS data provides the imagery exact placement for precise measurement and use with various mapping programs, chart plotters, GPS devices, and the like. The images may be manually assembled and processed to create the ortho-mosaic using Adobe Photoshop to show the precise location of the target plant colonies. A series of overlapping image files of the target plant colonies in various formats, such as JPEG, TIFF, and DNG, are gathered by the aerial platform 110.

The ortho-mosaic may be created in various formats, such as a TIFF file. The ortho-mosaic may then be uploaded to various mapping programs, such ArcGIS, Google Earth, and Map Plus as a shape file or an overlay in proper orientation, as shown in block 360. This allows a user to receive a ready-to-use map, video scan, or the like, that may be used to measure, navigate to, apply treatment to, and manage the respective target plant colonies. The generated maps may readily interact with equipment used by those responsible for assessing and treating aquatic plant infestations, such as chemical applicators, conservation districts, lake associations, and lake management companies. A such, the system 100 is used to help eradicate invasive species and/or vegetate plant life in contaminated portions of a body of water.

The implementation of the method 300 using the system 100 shown in FIG. 1 offers a number of advantages, including providing precise follow-up assessment and treatment of aquatic species through mapping or real-time aerial observation. Significant amount of time is saved and more accurate results are generated by not needing to interpolate areas between intersect points for areas being mapped. This results in few instances of false positives indicating plant mass in locations where it is not actually present. As a result, a more accurate and thorough amount of chemical application may be used to treat the water, causing less negative impact on the ecology. Since it is easier to locate aquatic plant infestations aerially than from the water level, visual verification of actual water conditions before and after treatment is greatly improved.

In some situations, such as those that require the identification of aquatic plants in deeper waters (having a depth of greater than or equal to 25 feet) and/or water having less clarity (greater turbidity or tannins), aerial detection of the aquatic plants may be very difficult. In these situations, the use of sonar and ground truthing in combination with at least one remotely operated underwater vehicle (ROV) provides a more reliable and effective solution. In these examples, sonar may be used to locate the aquatic plants and the ROV may be used to verify their presence. An ROV can take up close imagery, recorded or transmitted, for verification or plant identification.

Figure 4:
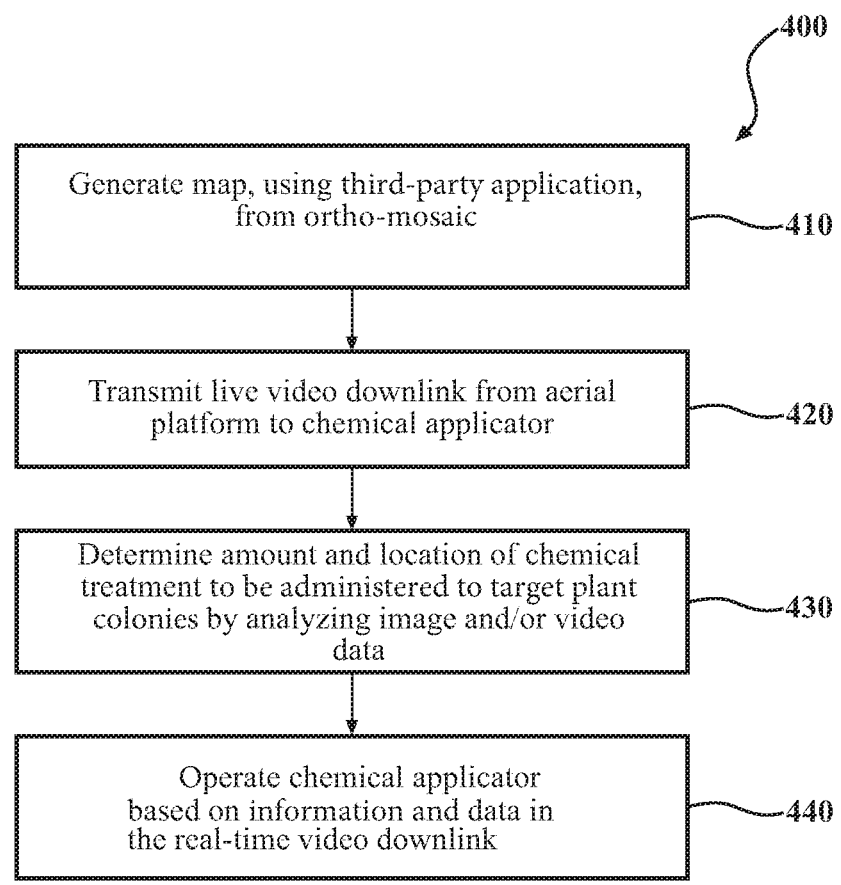
FIG. 4 is a flow chart of an exemplary method for providing real-time visual guidance to a chemical applicator using the system shown in FIG. 1.

Referring to FIG. 4, FIG. 4 shows a flow chart of an exemplary method 400 for providing real-time visual guidance to a chemical applicator using the system 100 shown in FIG. 1. In block 410, the aerial platform 110 captures, records, and maps a real-time visual image and/or video of a treatment area in a body of water. The operator of the aerial platform 110 then transmits a live video downlink to a chemical applicator, as shown in block 420. In some embodiments, the operator of the aerial platform 110 transmits the real-time video downlink using the controller 120 located on an operator vessel located outside of the treatment area. The operator vessel may about 21 feet about the surface of the water.

In block 430, the chemical applicator analyzes and interprets the image and/or video data provided by the operator of the aerial platform 110 to determine the amount and precise location of the chemical application treatment. The result is a more precise coverage of the target plants and more efficient use of the chemical application due to the fact that the chemical applicator can view the size, start, and end of the treatment area in advance of administration. In block 440, the chemical applicator vessel is specifically steered/operated based on the data provided in the real-time video downlink received from the operator of the aerial platform 110.

In some embodiments, an unmanned surface vehicle acting as a chemical applicator vessel, such as an open or sealed hull boat, can administer a chemical application to a targeted area in the water through remote aerial observation by the aerial platform 110 and GPS-aided autopilot. Thus, the chemical applicator vessel may be remotely operated by the operator of the aerial platform 110. Data gathered from the aerial platform 110 can be used to plan a mission for the unmanned surface vehicle. A remote signal from the operator triggers the administration of a specific chemical into targeted locations in the water. The remote control may be either a radio signal or a tethered data cable. As a result, the crew on the chemical applicator vessel is entirely removed from any unnecessary exposure to toxic chemicals.

Figure 5:
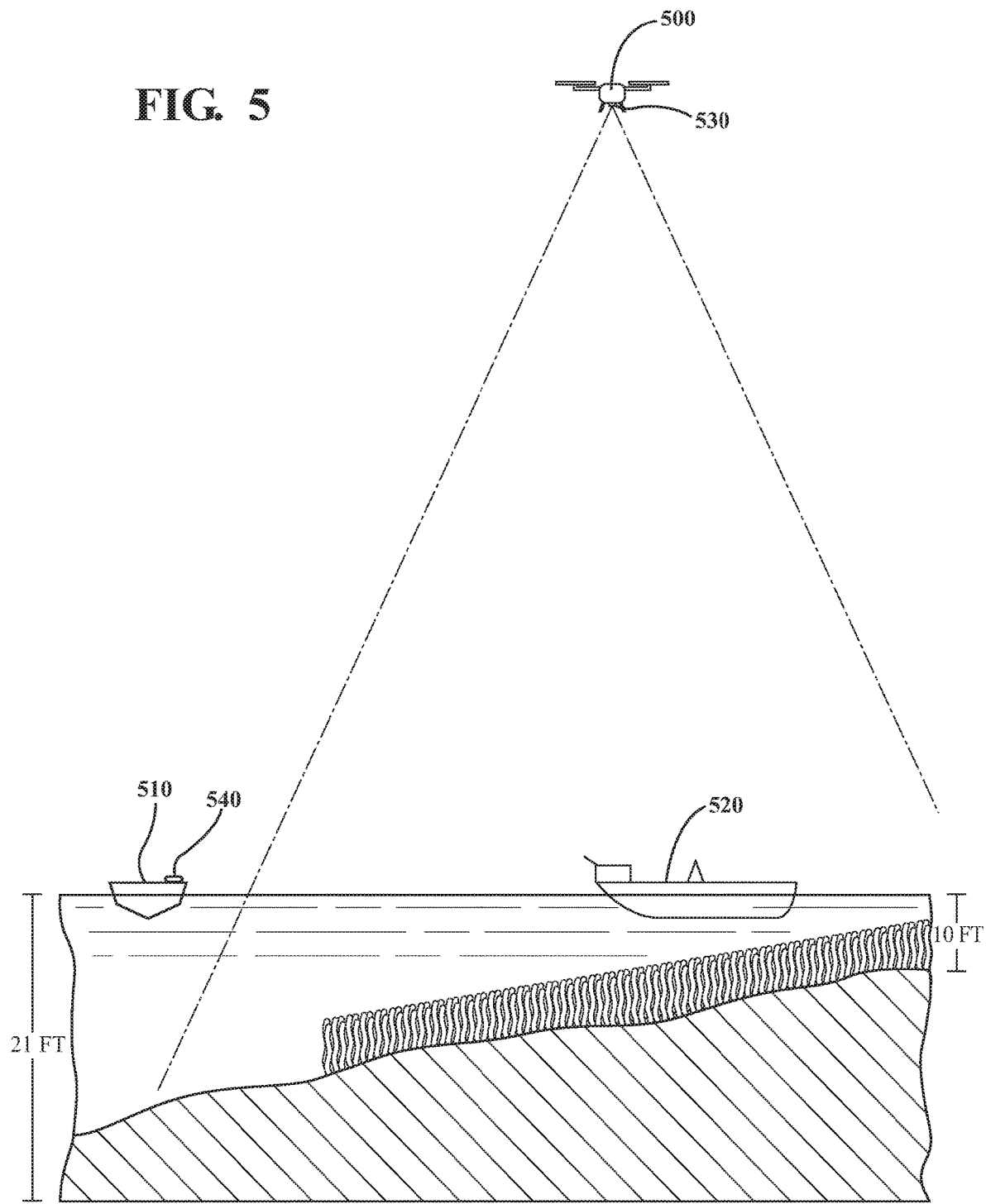
FIG. 5 is another exemplary embodiment for providing real-time visual guidance to a chemical applicator.

Referring to FIG. 5, FIG. 5 shows another exemplary embodiment for providing real-time visual guidance to a chemical applicator. FIG. 5 also depicts a UAV 500, an operator vessel 510, and a chemical applicator vessel 520. The UAV 500 comprises a sensor assembly 530, which detects aquatic plant species located in the field of view of the sensor assembly 130. The angle of view of the sensor assembly 130 may be at an angle of less than or about 360°, 240°, 120°, 90°, 30°, or 10°. In some examples, the sensor assembly 530 comprises an electro-optical sensor with a polarizer (not shown), the electro-optical sensor may be positioned about 131 feet above the surface of the water and has an angle of view of about 92°. Thus, the view results in about a 10,000-square foot area of coverage.

The operator vessel 510 comprises a controller 540, the controller 540 is configured to command the UAV 500 to move; capture images and/or video of the desired aquatic environment; and to transmit the images and/or video to the controller 540. The operator of the operator vessel 510 may then transmit a real-time video downlink of the captured aquatic environment to the chemical applicator in the chemical applicator vessel 520, which is located in the intended treatment area of the aquatic environment. In this embodiment, the operator vessel 510 is located outside the intended treatment area of the aquatic environment.

Using the real-time video downlink, the chemical applicator may readily visualize the size and scope of the intended treatment area. As a result, the chemical applicator can more quickly, accurately, and efficiently apply a specific chemical to the intended treatment area. The chemical applicator navigates the chemical applicator vessel 520 based on the specific information visualized in the real-time video downlink.

Figure 6:
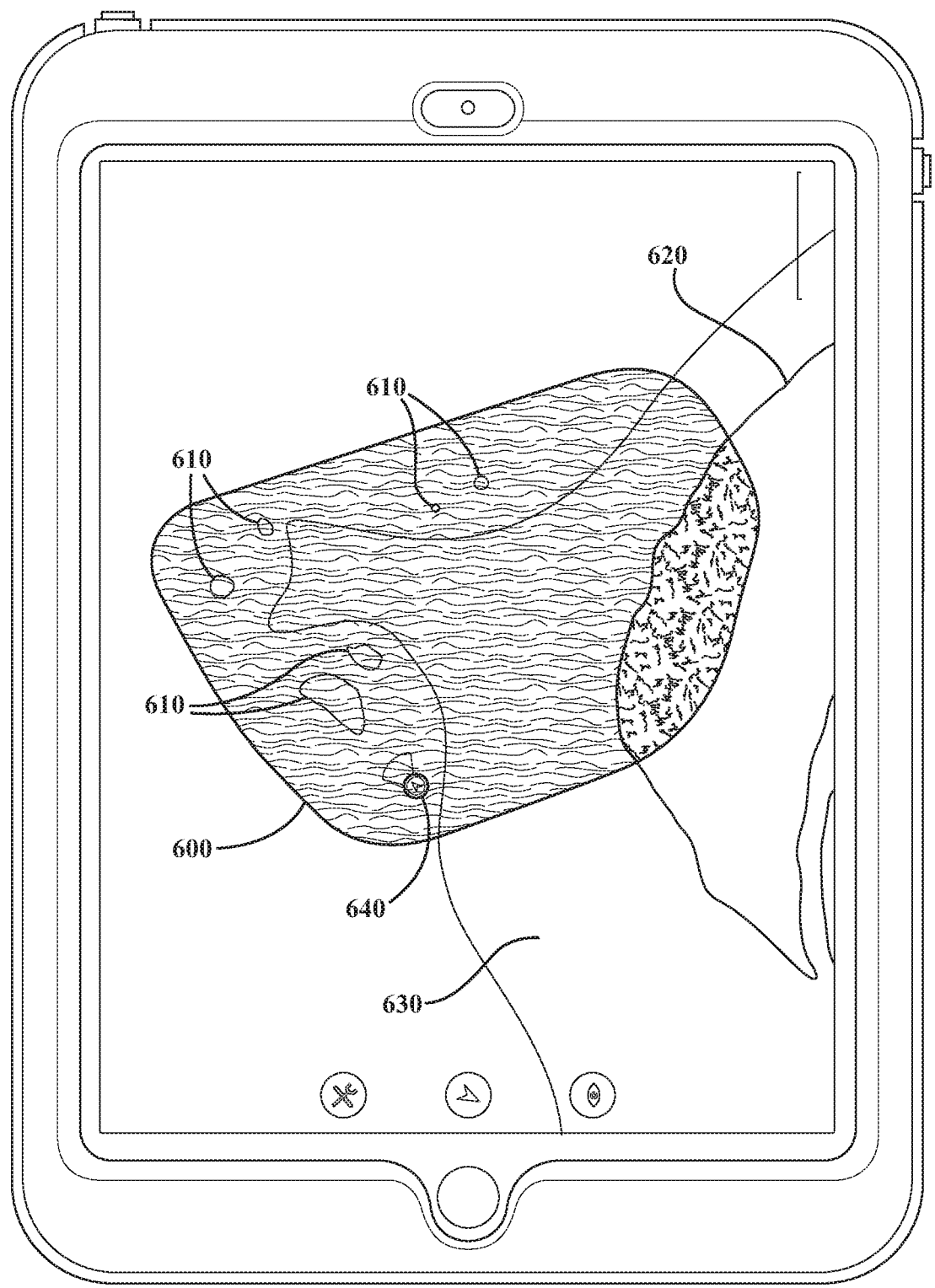
FIG. 6 is an image of an exemplary ortho-mosaic overlay generated by the system shown in FIG. 1.

Referring to FIG. 6, FIG. 6 shows an image of an exemplary ortho-mosaic overlay 600 generated by the system 100 shown in FIG. 1. In this embodiment, the ortho-mosaic overlay 600 is displayed via a mapping application, such as Google Earth or Map Plus, on a tablet. The ortho-mosaic overlay 600 of FIG. 6 displays the surveyed area, which includes the location of any submergent or emergent target species, such as aquatic plant colonies 610. In FIG. 6, the mapping application also displays the location of a shoreline 620, a sand bar 630, and a vessel 640. The ortho-mosaic overlay 600 may be used for GPS navigation on tablets or other mobile computing devices, such as phones, watches, laptops, and the like, that have a data plan or that are tethered to a hot spot or a smart phone. The mobile computing devices may be of any platform, such as Android, iOS, RIM, etc.

Figure 7:
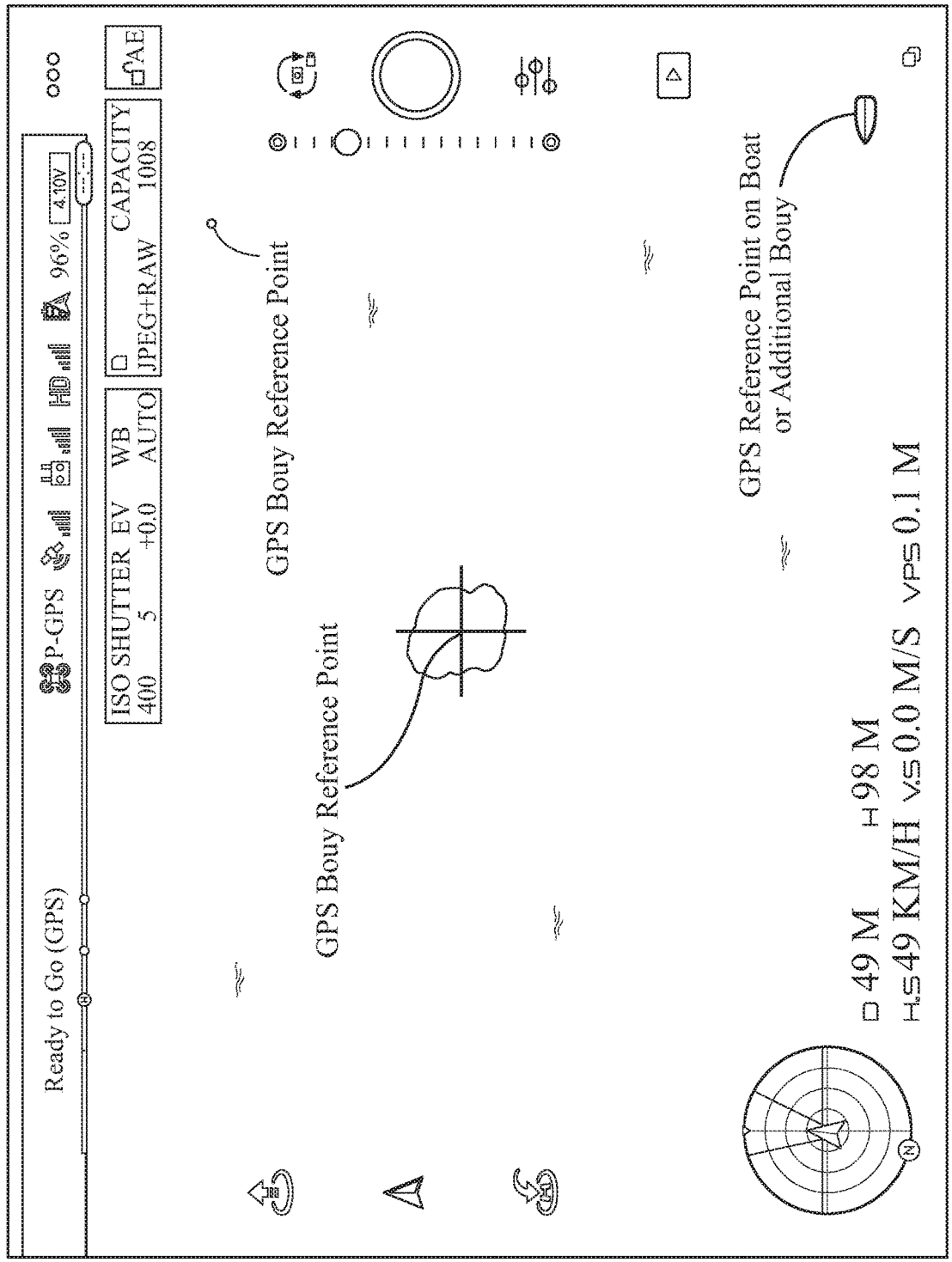
FIG. 7 is an image of an exemplary grid and triangulation capture by the aerial platform.

Referring to FIG. 7, FIG. 7 shows an image of an exemplary grid and triangulation capture by the aerial platform 110. The grid shows the ability of the aerial platform 110 to capture imagery where natural ground reference points are not available. Instead of using natural ground reference points, a GPS reference point generated by the electro-optical sensor 200 is taken from the nadir position as a GPS reference point on a first buoy, and a GPS reference point on a boat or a second buoy may be incorporated by the system 100 for mapping with precise scale and positioning. The GPS buoy reference point is used for triangulation. The grid displayed herein provide quick visual estimates of size by area to an intended user.

Figure 8:
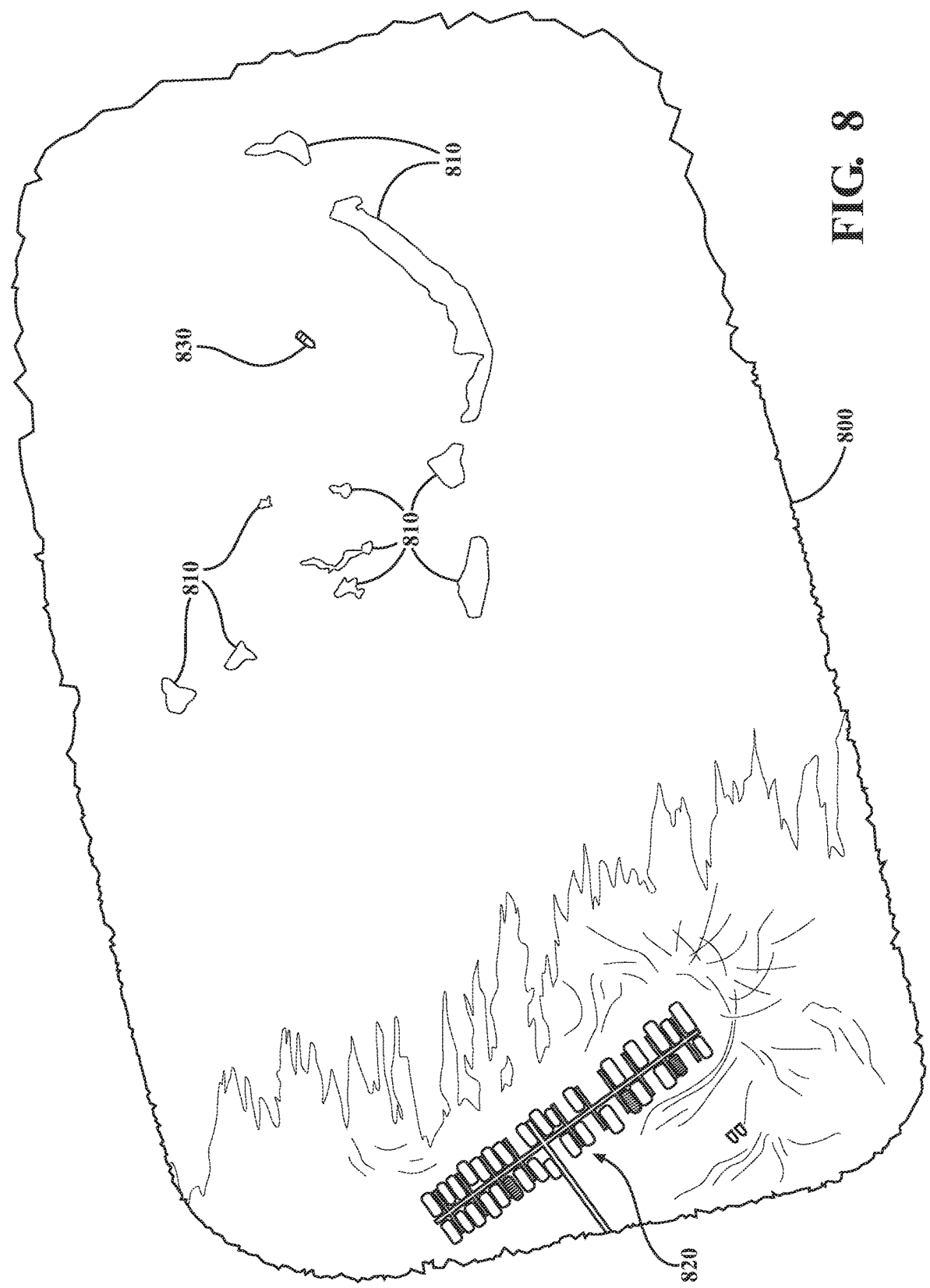
FIG. 8 is an image of an exemplary ortho-mosaic overlay on Google Maps™ captured by the aerial platform.

Referring to FIG. 8, FIG. 8 shows an image of an exemplary ortho-mosaic overlay 800 on Google Maps™ captured by the aerial platform 110. This geotagged image specifically shows the precise areas of aquatic plant colonies 810, such as Eurasian Water milfoil and other aquatic plant species in the water for exact measurement. The aquatic plant colonies 810 are displayed in relation to a marina 820 and a vessel 830.

It will, of course, be understood that, although particular embodiments have just been described, the claimed subject matter is not limited in scope to a particular embodiment or implementation. Likewise, an embodiment may be implemented in any combination of systems, methods, or products made by a process, for example.

In the preceding description, various aspects of claimed subject have been described. For purposes of explanation, specific numbers, systems, and/or configurations were set forth to provide a thorough understanding of claimed subject matter. Computer file types and languages, and operating system examples have been used for purposes of illustrating a particular example. However, it should be apparent to one skilled in the art having the benefit of this disclosure that claimed subject matter may be practiced with many other computer languages, operating systems, file types, and without these specific details. In other instances, features that would be understood by one of ordinary skill were omitted or simplified so as not to obscure claimed subject matter. While certain features have been illustrated or described herein, many modifications, substitutions, changes or equivalents will now occur to those skilled in the art. It is, therefore, to be understood that claims are intended to cover all such modifications or changes as fall within the true spirit of claimed subject matter.

Likewise, an example may be implemented in any combination of compositions of matter, apparatuses, methods or products made by a process, for example. The following examples are merely representative of methods of practicing one or more embodiments of the present invention and should not be read as limiting the scope of the invention.

The invention claimed is:

1. A method for visually detecting and mapping the presence of a target species located beneath the surface of a body of water, the method comprising:
   calibrating a camera and at least one sensor on an unmanned aerial vehicle to record light wave reflectance values from the target species, wherein the target species is located at least about 5 feet beneath the surface of the body of water;
   scanning, using the unmanned aerial vehicle, the body of water to identify the location of the target species;
   capturing in real-time, using the camera, at least one image or video of the body of water;
   recording, using the at least one sensor, data corresponding to the at least one image or video on the unmanned aerial vehicle;
   detecting the presence of the target species in the body of water and obtaining a ground truth sample of the target species when the target species is present in the body of water;
   transmitting the at least one image or video from the unmanned aerial vehicle to a software application;
   assembling and processing the at least one image or video to create an ortho-mosaic, wherein the ortho-mosaic displays the precise location of the target species beneath the surface of the water; and
   generating a map showing the location of the target species in the body of water.

2. The method of claim 1, wherein prior to recording data corresponding to the at least one image or video on the unmanned aerial vehicle, geotagging the at least one image or video.

3. The method of claim 1, wherein the target species is an invasive aquatic plant.

4. The method of claim 1, wherein the at least one sensor comprises an electro-optical sensor, a light imaging, detection, and ranging (LIDAR) sensor, a near infrared (NIR) sensor, a multispectral sensor, or any combination thereof.

5. The method of claim 1, wherein calibrating the at least one sensor on the unmanned aerial vehicle comprises determining at least one angle of view and at least one field of view of the at least one sensor with respect to the body of water.

6. The method of claim 5, wherein the angle of view is between about 80 and 120 degrees.

7. The method of claim 1, further comprising transmitting the map to a chemical applicator, wherein the chemical applicator is configured to apply a chemical treatment to the target species.

8. A system for visually detecting and mapping the presence of a target species located beneath the surface of a body of water, the system comprising:
   an unmanned aerial vehicle, wherein the unmanned aerial vehicle is configured to scan the body of water to identify the location of the target species beneath the surface of the water, wherein the target species is located at least about 5 feet beneath the surface of the body of water;
   a camera and at least one sensor on the unmanned aerial vehicle, wherein the camera is configured to capture at least one image or video of the body of water in real-time and wherein the at least one sensor is configured to record data corresponding to the at least one image or video; and
   a controller in direct communication with the unmanned aerial vehicle, wherein the controller is configured to control the position and orientation of the unmanned aerial vehicle with regard to the body of water and to display data, images, and videos received from the unmanned aerial vehicle.

9. The system of claim 8, wherein the target species is an invasive aquatic plant.

10. The system of claim 8, wherein at least one sensor comprises an electro-optical sensor, a light imaging, detection, and ranging (LIDAR) sensor, a near infrared (NIR) sensor, a multispectral sensor, or any combination thereof.

11. The system of clam 8, wherein the system further comprises a chemical applicator in direct communication with the unmanned aerial vehicle, wherein the chemical applicator is configured to receive, analyze, and process data and information from the unmanned aerial vehicle and to apply a chemical treatment to the body of water.

12. The system of claim 11, wherein the data and information is transmitted to the chemical applicator via a real-time video downlink.

13. The system of claim 11, wherein the chemical applicator comprises an unmanned surface vehicle.

14. The system of claim 13, wherein the unmanned aerial vehicle and the chemical applicator are both remotely operated by the same operator.

* * * * *